United States Patent
Hancu et al.

(10) Patent No.: US 6,710,192 B2
(45) Date of Patent: Mar. 23, 2004

(54) DENSE PHASE EPOXIDATION

(75) Inventors: Dan Hancu, Secane, PA (US); Eric John Beckman, Aspinwall, PA (US); Tiberiu Danciu, Pittsburgh, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/981,198

(22) Filed: Oct. 16, 2001

(65) Prior Publication Data

US 2003/0073856 A1 Apr. 17, 2003

(51) Int. Cl.⁷ .............................................. C07D 303/00
(52) U.S. Cl. ........................................................ 549/512
(58) Field of Search .......................................... 549/512

(56) References Cited

U.S. PATENT DOCUMENTS

| | | |
|---|---|---|
| 4,408,081 A | 10/1983 | Foster |
| 4,408,082 A | 10/1983 | Baumgartner |
| 5,744,619 A | 4/1998 | Nemeth et al. |
| 5,780,654 A | 7/1998 | Nemeth et al. |
| 6,005,123 A | 12/1999 | Dessau et al. |
| 6,008,388 A | 12/1999 | Dessau et al. |

FOREIGN PATENT DOCUMENTS

| | | | |
|---|---|---|---|
| BE | 1001038 | 6/1989 | |
| JP | 4-352771 | 12/1992 | |
| WO | WO99/64376 | 11/1999 | ............... 549/512 |

OTHER PUBLICATIONS

Pesiri et al, "selective epoxidation in dense phase carbon dioxide", Chem. Commun. 1998 No. 9, pp 1015–1016 (1998).*

Jenzer etal "Epoxidation of propylene with oxygen and hydrogen on a Pd–Pt/TS–1 catalyst" Applied catalysis. vol. 208 (1,2) pp. 125–133, Feb. 14, 2001.

* cited by examiner

*Primary Examiner*—Patricia L. Morris
*Assistant Examiner*—Raymond Covington
(74) *Attorney, Agent, or Firm*—William C. Long

(57) ABSTRACT

Propylene oxide is formed by reaction of hydrogen, oxygen, and propylene over a solid catalyst such as Pd on TS-1, the reaction being carried out in carbon dioxide solvent at conditions effective to provide a dense phase reaction mixture.

4 Claims, No Drawings

DENSE PHASE EPOXIDATION

FIELD OF THE INVENTION

The present invention relates to the epoxidation of an olefin such as propylene by reaction with hydrogen and oxygen using a solid catalyst such as Pd on TS-1, the improvement being that the reaction is carried out in carbon dioxide solvent under dense reaction mixture phase conditions.

BACKGROUND OF THE INVENTION

Epoxides constitute an important class of chemical intermediates useful for the preparation of polyether polyols, glycols, glycol ethers, surfactants, functional fluids, fuel additives and the like. Many different methods for synthesizing epoxides from the corresponding olefins have been described in the literature. A Japanese patent application assigned to the Tosoh Corporation and published in 1992 (Kokai No. 4-352771) proposed making propylene oxide by reacting propylene, hydrogen and oxygen using a catalyst comprising a Group VIII metal and a crystalline titanosilicate.

As with any chemical process, it would be desirable to attain further improvements in epoxidation methods of this type.

Dense phase reaction mixture conditions have been employed in various reaction systems, most notably in the production of tertiary butyl hydroperoxide by direct oxidation of isobutene. See, for example, U.S. Pat. Nos. 4,408,081 and 4,408,082.

SUMMARY OF THE INVENTION

In accordance with the present invention, the epoxidation is carried out by reacting olefin, hydrogen and oxygen using a noble metal on titanium or vanadium zeolite catalyst, the improvement being that the reaction is carried out using $CO_2$ as the essential solvent at dense phase reaction conditions.

DETAILED DESCRIPTION

There are a number of significant advantages which are achieved through practice of the present invention. $CO_2$ is the essential solvent used for the reaction and accordingly solvolysis of the oxirane product is suppressed due to the absence of any nucleophile species except for water of reaction. Leaching of noble metal from the solid catalyst is minimal due to insolubility in $CO_2$. Because the olefin, hydrogen and oxygen are totally miscible in the dense phase system, better control of the reagent concentrations can be achieved and the dead space in the reactor can be substantially eliminated.

In general, reagents and catalysts previously taught for this reaction can be used. In this regard, reference is made to prior teachings such as Kokai No. 4-352771 above referred to as well as U.S. Pat. Nos. 6,005,123 and 6,008,388, the disclosure's of which are incorporated herein by reference.

The catalysts to be used in the present process are comprised of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The choice of zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite or vanadium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2 (1-x)Sio_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent. The manner in which the noble metal is incorporated into the catalyst is not considered to be particularly critical. For example, the noble metal may be supported on the zeolite by impregnation means or the like or first supported on another substance such as silica, alumina, activated carbon or the like and then physically mixed with the zeolite. Alternatively, the noble metal can be incorporated into the zeolite by ion-exchange with, for example, Pd tetraamine chloride with or without added ammonium hydroxide. The catalyst is recovered by filtration and washing and is substantially free (<0.1 wt. %) of halide. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals. Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the catalyst may be fully or partially pre-reduced. Satisfactory catalytic performance can, however, be attained without any pre-reduction whatsoever. To achieve the active state of palladium, the catalyst may undergo pretreatment such as thermal treatment in nitrogen, vacuum, hydrogen or air.

The catalyst may additionally comprise a binder or the like and may be molded, stray dried, shaped or extruded into any desired form prior to use in epoxidation. In addition to the noble metal, the catalyst may be modified with additional elements such as, for example, lanthanide metals (e.g., europium) iron, cobalt, nickel, boron, aluminum, phosphorus, calcium, vanadium, chromium, manganese, copper, zinc, and gallium.

The olefin to be used can be any organic compound containing at least one site of ethylenic unsaturation (i.e., at least one carbon-carbon double bond). The olefin can be aliphatic, aromatic or cycloaliphatic in character and may have either a linear or branched structure, with the site(s) of theylenic unsaturation being terminal and/or internal. The olefin preferably contains 2–30 carbon atoms; the process of the invention is particularly suitable for expoxidizing $C_2$–$C_6$ mono-olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro, groups or the like.

Typical examples of suitable olefins include ethylene, propylene, 1-butene, cis- and trans-2-butene, isobutene, 1,3-butadiene, pentenes, isoprene, hexenes, octanes, nonenes, decenes, undecenes, dodecenes, cyclopentene, cyclohexene, dicyclopentadiene, vinylcylohexane, vinylcyclohexene, allyl chloride, allyl alcohol, methallyl chloride, methallyl alcohol, alkyl acrylates and methacrylates, unsaturated fatty acids and esters thereof, styrene, alpha methylstyrene, divinylbenzene, indene and stilbene. Mixtures of olefins may, of course, be utilized if so desired. The process of this invention is especially useful for converting propylene to propylene oxide.

The epoxidation reaction is carried out using $CO_2$ as essential solvent, at conditions which are effective to provide a single dense phase reaction mixture. Although small amounts of other solvents can be tolerated it is preferred that $CO_2$ comprise the major amount and preferably at least 98% by weight of the reaction solvent. The $CO_2$ solvent comprises at least about 10 wt % of the reaction mixture, preferably about 75% or more up to 95% or more.

A dense-phase feed reaction mixture is one maintained at a pressure sufficiently elevated so that the mixture of olefin —$CO_2$—$O_2$—$H_2$ is a single, dense, liquid-like phase with a density higher than 0.25 g/cm$^3$. Suitable temperatures are in the range of 20 to 100° C. and suitable pressures from 10 to 300 atm. In other words, the dense-phase reaction mixture is free of the vapor phase, which has been characteristic of prior art reaction in the vapor phase or in a two phase (vapor-liquid) mixture. Preferably, the feed reaction mixture is under supercritical conditions, that is, a mixture comprising of olefin, oxygen, hydrogen, $CO_2$ maintained above its critical temperature as well as above its critical pressure. The oxygen and hydrogen are present in solution in the dense phase mixture, not as a separate vapor phase.

Although the critical points of temperature and pressure of $CO_2$ of 31.1° C. and 72.9 atm are useful in establishing conditions for carrying out the reaction in accordance with the invention, actually the critical temperature of the feed solution, for example propylene in $CO_2$, is between 31.1° C. and 91.9° C. (Tc of propylene) and the critical pressure is higher than 46.2 atm (Pc of propylene). In the case of propylene epoxidation, suitable operating conditions are pressure of 15 to 300 atm and temperatures of 20 to 100° C. The molar ratio of hydrogen to oxygen can usually be varied in the range of $H_2:O_2$=1:10 to 5:1 and is especially favorable at 1:5 to 2:1. The molar ratio of oxygen to olefin is usually 1:1 to 1:20, and preferably 1:1.5 to 1:10.

The following examples illustrate practice of the invention.

EXAMPLE 1

Preparation of Pd/TS-1 Catalyst

Pd was supported on TS-1 by suspending TS-1 (1.6% Ti, 20 grams) in deionized water (80 grams), in the presence of tetraamine palladium nitrate (5% Pd, 2.542 grams) at 80° C. for 24 hours. The solid was recovered by filtration under pressurized $N_2$, washed with deionized water (150 mL, three times), dried under house vacuum at 50° C. overnight, and calcined at 150° C. for 4 hrs in 5% $O_2$-95% $N_2$ mixture. The resulting catalyst has 0.47 wt % Pd. Pd/TS-1 catalyst (2 grams) was then suspended in 75 wt % MeOH -25 wt % $H_2O$ (100 grams) and preactivated in a 100 cc/min gas flow (10% $C_3H_6$, 4% $O_2$, and 4% $H_2$) at 45 C. and 3 psig for 22 hours.

EXAMPLE 2

Preparation of Pd/TS-1 Catalyst

The same procedure is carried out as in Example 1 using 0.8 grams of tetraamine palladium nitrate (5% Pd). The resulting catalyst has 0.31 wt % Pd.

EXAMPLE 3

Synthesis of Propylene Oxide in Dense Phase Reaction Mixture

The reaction was carried out in a stainless steel batch reactor (volume 38.4 cm$^3$) connected to a high pressure syringe pump (High Pressure Equipment, 30 cm$^3$), high pressure recirculating pump and a Hewlett Packard 5890 Series 2 Gas Chromatograph, featuring both TCD and FID detectors. Pd/TS-1 (0.1512 g) prepared in Example 1 was charged to the reactor (38.4 cm$^3$) and then the system was thoroughly evacuated under vacuum. The reactor is heated at 45° C. and known amounts of $CO_2$ (60.9 mmol), $H_2$ (1.26 mmol), air (31.3 mmol) and propylene (3.97 mmol) are added (in this order) to the high pressure batch reactor. Additional super critical $CO_2$ (Praxair, Coolant grade, 548 mmol) is added via a gas booster (single stage, Haskel) to reach 1900 psig, to provide a dense phase reaction mixture, and the reaction mixture is vigorously mixed for 4.5 hours. At the end of run, the dense phase is first analyzed by GC and then slowly depressurized to atmospheric pressure. The possible side products precipitated on the solid catalyst are extracted in 5 mL MeOH and analyzed separately by GC. After 4.5 hours the overall productivity was 0.0256 g propylene oxide/g cat.xhour while propylene selectivity to propylene oxide was 62.1% No propylene glycol or other ring opening products were detected.

EXAMPLE 4

Synthesis of Propylene Oxide in Dense Phase Reaction Mixture

Propylene (3.97 mmol), hydrogen (1.26 mmol) and oxygen (5.94 mmol—from air) were added in the reactor to form propylene oxide as described in Example 3. The catalyst was Pd/TS-1, prepared in Example 2 in amount of 0.1952 grams. About 26.76 grams of $CO_2$ were charged as solvent and the reaction was carried out in the dense phase at 1895 psig and 45° C. After three hours the overall productivity was 0.0159 g propylene oxide/g cat×hour while propylene selectivity to PO was 91.2%. No propylene glycol or other ring opening products were detected.

Comparative Example 5

Synthesis of Propylene Oxide in $CO_2$—$H_2O$—MeOH

The reaction was conducted in the experimental setup described in Example 3. Pd/TS-1 (0.1565 g) prepared in Example 1, water (2.5 g) and MeOH (7.5 g, Aldrich, absolute) were charged to the reactor (38.4 cm³). The reactor is heated at 45° C., and known amounts of $CO_2$ (41.3 mmol), $H_2$ (1.26 mmol), air (31.3 mmol) and propylene (3.97 mmol) are added (in this order) to the high pressure batch reactor. Additional supercritical $CO_2$ (Praxair, Coolant grade, 372 mmol) is added via a gas booster (single stage, Haskel) to reach 1860 psig, and the reaction mixture is vigorously mixed for 4.5 hours. At the end of run, the $CO_2$ phase is first analyzed by GC and then slowly depressurized to atmospheric pressure. The resulting slurry is filtered and the filtrate is analyzed by GC. After 4.5 hours the overall propylene oxide productivity was 0.00186 g propylene oxide/g cat×hour while propylene selectivity to propylene oxide was 18.8%. Traces of 1-methoxy-propane-2-ol (30 ppm, PM1), 2-methoxy-propane-1-ol (50 ppm, PM2) and methyl formate (240 ppm) were detected in the resulting methanol solution.

Comparative Example 6

Synthesis of Propylene Oxide in $H_2O$—MeOH

The reaction was conducted in the experimental setup described in Example 3. Pd/TS-1 (0.1977 g) prepared in Example 1, water (2.5 g) and MeOH (7.5 g, Aldrich absolute) were charged to the autoclave. The reactor is heated at 45° C. and known amounts of $N_2$ (7.4 mmol), $H_2$ (1.26 mmol), air (31.3 mmol) and propylene (3.97 mmol) are added (in this order) to the high pressure batch reactor. Additional $N_2$ (Praxair UHP/ZERO grade, 120 mmol) is added to reach 2000 psig, and the reaction mixture is vigorously mixed for 4.5 hours. At the end of run, the gas phase is first analyzed by GC and then slowly depressurized to atmospheric pressure. The resulting slurry is filtered and the filtrate is analyzed by GC. After 4.5 hours the overall propylene oxide productivity was 0.00516 g propylene oxide/g cat×hour while propylene selectivity to propylene oxide was 6.4%. Traces of 1-methoxy-propane-2-ol (30 ppm PM1), 2-methoxy-propane-1-ol (50 ppm, PM2) and methyl formate (240 ppm) were detected in the resulting methanol solution.

EXAMPLE 7

Propylene Oxide Solvolysis in Supercritical $CO_2$

The reaction was conducted in the experimental setup described in Example 3. Pd/TS-1 (0.3044 g) prepared in Example 2, water (0.12 g) and propylene oxide (0.4316 g) were charged to the autoclave. Supercritical $CO_2$ (30.9 g) is added to reach 2780 psig, and the reaction mixture is vigorously mixed at 45° C. for 4.5 hours. At the end of the run, the reaction mixture is analyzed by GC and then, the system is slowly depressurized to atmospheric pressure. The possible ring opening products are extracted in 10 mL MeOH and analyzed separately by GC. After 4.5 hours, no propylene glycol was detected.

EXAMPLE 8

PO Solvolysis in MeOH—$H_2O$

The reaction was conducted in the experimental setup described in Example 3. Pd/TS-1 (0.3039 g) prepared in Example 2, water (1.65 g), methanol (5 g) and propylene oxide (0.3486 g) were charged to the autoclave. $N_2$ is added to reach 2180 psig, and the reaction mixture is vigorously mixed at 45° C. for 4.5 hours. At the end of the run both the gas and liquid phases are analyzed by GC, and the system is then slowly depressurized to atmospheric pressure. After 4.5 hours, the percentage of PO reacted with MeOH/$H_2O$ to form PM1, PM2 or propylene glycol (PG) was 60%.

The above examples demonstrate the outstanding improvements achieved through practice of the invention as compared to analogous procedures not according to the invention.

We claim:

1. In a process for the epoxidation of an olefin by contacting hydrogen, oxygen and olefin at reactive conditions with a solid insoluble epoxidation catalyst comprised of noble metal on titanium or vanadium silicalite, the improvement which comprises carrying out the epoxidation in carbon dioxide solvent at conditions effective to provide a dense phase reaction mixture.

2. In a process for the epoxidation of propylene by contacting hydrogen, oxygen and propylene at reactive conditions with a solid insoluble epoxidation catalyst comprised of noble metal on TS-1, the improvement which comprises carrying out the epoxidation in carbon dioxide solvent at conditions effective to provide a dense phase reaction mixture.

3. The process of claim 1 wherein the catalyst is Pd on TS-1.

4. The process of claim 1 wherein the reaction conditions are a temperature of 20 to 100° C. and a pressure of 10–300 atm.

* * * * *